United States Patent
Drizen et al.

(10) Patent No.: US 9,821,005 B2
(45) Date of Patent: Nov. 21, 2017

(54) POLYMER MATRIX COMPOSITIONS COMPRISING A HIGH CONCENTRATION OF BIO-FERMENTED SODIUM HYALURONATE AND USES THEREOF

(71) Applicant: GlycoBioSciences Inc., Georgetown (CA)

(72) Inventors: Kevin Drizen, Georgetown (CA); Jai Velusamy, Mississauga (CA)

(73) Assignee: GLYCOBIOSCIENCES INC., Georgetown, Ontario (CA)

( * ) Notice: Subject to any disclaimer, the term of this patent is extended or adjusted under 35 U.S.C. 154(b) by 0 days.

(21) Appl. No.: 14/818,810

(22) Filed: Aug. 5, 2015

(65) Prior Publication Data

US 2017/0020912 A1    Jan. 26, 2017

(30) Foreign Application Priority Data

Jul. 23, 2015 (EP) ...................... 15178106

(51) Int. Cl.

| | | |
|---|---|---|
| A61K 31/728 | (2006.01) | |
| A61L 26/00 | (2006.01) | |
| A61K 47/38 | (2006.01) | |
| A61K 47/10 | (2017.01) | |
| A61K 9/00 | (2006.01) | |
| A61K 31/047 | (2006.01) | |
| A61K 31/196 | (2006.01) | |
| A61K 47/14 | (2017.01) | |
| A61K 45/06 | (2006.01) | |
| A61K 31/197 | (2006.01) | |
| A61K 31/455 | (2006.01) | |
| A61K 9/06 | (2006.01) | |
| A61K 47/36 | (2006.01) | |

(52) U.S. Cl.
CPC .......... *A61K 31/728* (2013.01); *A61K 9/0014* (2013.01); *A61K 9/0034* (2013.01); *A61K 9/06* (2013.01); *A61K 31/047* (2013.01); *A61K 31/196* (2013.01); *A61K 31/197* (2013.01); *A61K 31/455* (2013.01); *A61K 45/06* (2013.01); *A61K 47/10* (2013.01); *A61K 47/14* (2013.01); *A61K 47/36* (2013.01); *A61K 47/38* (2013.01); *A61L 26/008* (2013.01); *A61L 26/0023* (2013.01); *A61L 26/0052* (2013.01); *A61L 26/0066* (2013.01)

(58) Field of Classification Search
CPC ...... A61K 31/728; A61K 47/38; A61K 47/10; A61K 9/0014; A61K 9/0034; A61K 9/06; A61L 26/0023; A61L 26/0052; A61L 26/0066; A61L 26/008
See application file for complete search history.

(56) References Cited

U.S. PATENT DOCUMENTS

| | | |
|---|---|---|
| 3,652,762 A | 3/1972 | Pfister et al. |
| 4,517,295 A | 5/1985 | Bracke et al. |
| 4,782,046 A | 11/1988 | Brown et al. |
| 4,801,539 A | 1/1989 | Akasaka et al. |
| 5,897,880 A | 4/1999 | Drizen et al. |
| 6,007,843 A | 12/1999 | Drizen et al. |
| 6,063,405 A | 5/2000 | Drizen et al. |
| 6,120,804 A | 9/2000 | Drizen et al. |
| 6,335,035 B1 | 1/2002 | Drizen et al. |
| 6,387,407 B1 | 5/2002 | Drizen et al. |
| 6,723,345 B2 | 4/2004 | Drizen et al. |
| 2008/0119437 A1* | 5/2008 | Lewis .................. A61K 8/735 514/54 |

FOREIGN PATENT DOCUMENTS

| | | |
|---|---|---|
| EP | 0 244 757 | 11/1994 |
| WO | 198604355 | 7/1986 |
| WO | 9208799 | 5/1992 |
| WO | 2003054163 | 7/2003 |
| WO | 2008094910 | 8/2008 |
| WO | 2010011605 | 1/2010 |
| WO | 2014165971 | 10/2014 |

OTHER PUBLICATIONS

Internet Archive Wayback Machine, https://web.archive.org, accessed online on Feb. 14, 2017.*
Smolinske, S.C., CRC Handbook of Food, Drug, and Cosmetic Excipients, 1992, CRC Press LLC, p. 287-289.*
Dow CarbowaxTM brochure, Dow Chemical Company, 2011, p. 1-12.*
European Pharmacopoeia 7.0, 2011, edition 7.0, section 5.1.4, p. 507.*
FDA Guidance for Industry Pyrogen and Endotoxins Testing: Questions and Answers, Jun. 2012, p. 1-10.*
Zange et al., Eur. J. Pharm. Biopharm., 1997, 44, p. 149-157.*
Becker et al., Int. J. Toxicol., 2009, 28(4S), p. 5-67 (Year: 2009).*
Chen et al. Wound Repair Regen. Mar.-Apr. 1999; 7(2): 79-89.
501k Clearance K123193 (IPM Wound Gel Bio) United States Food & Drug Administration, Mar. 3, 2014.
Ronald Reece Skin Ulcer therapy with hyaluronic acid tested—Pilot study of gel results in rapid healing of ulcers Oct. 1, 2000 Dermatology Times.

* cited by examiner

*Primary Examiner* — Jonathan S Lau
(74) *Attorney, Agent, or Firm* — Kevin Drizen; Glycobiosciences Inc.

(57) ABSTRACT

The present invention relates to stable polymer matrix compositions comprising high concentrations (from about 1.5% w/w to about 3.5% w/w) sodium hyaluronate obtained from a *Streptococcus zooepidemicus* source and a non-ionic polymer. The polymer matrix composition further comprises polyethylene glycol and methylparaben, and utilizes ingredients that are of pharmaceutical or compendial grade. The polymer matrix compositions may optionally comprise an active ingredient. The present polymer matrix compositions may be used in the treatment of wounds, burns, certain dermatological conditions, vaginal dryness, and in topical, transdermal delivery and sustained release of active ingredients.

5 Claims, No Drawings

POLYMER MATRIX COMPOSITIONS COMPRISING A HIGH CONCENTRATION OF BIO-FERMENTED SODIUM HYALURONATE AND USES THEREOF

FIELD OF THE INVENTION

The present invention relates to polymer matrix compositions comprising sodium hyaluronate. More particularly, the present invention relates to polymer matrix compositions comprising sodium hyaluronate obtained from a bacterial source and that are useful in the treatment of wounds and incisions, treatment of pain, transdermal delivery of active ingredients, sustained release of active ingredients, and preparation of personal lubricants.

BACKGROUND OF THE INVENTION

Hyaluronic acid (HA) is a naturally occurring mucopolysaccharide (also commonly referred to as glycosaminoglycan). It has been isolated by various methods from numerous tissue sources including vitreous humor, skin, synovial fluid, serum, chicken combs, shark skin, umbilical cords, tumors, hemolytic streptococci from pigskin, whale cartilage, and the walls of veins and arteries. HA may, however, also be synthesized artificially or made by recombinant technology. Moreover, it is known that HA may also be manufactured by fermentation of selected *Streptococcus zooepidemicus* bacterial strains (see U.S. Pat. No. 4,517,295 issued to Bracke et al.), and can readily be converted to its sodium salt. The repeating unit of the HA molecule is a disaccharide consisting of D-glucuronic acid and N-acetyl-D-glycosamine. Because HA has a negative charge at neutral pH, it is soluble in water, where it forms highly viscous solutions.

Fractions of HA, including its sodium salt, are known to form a stable polymer matrix when combined with a non-ionic polymer such as hydroxyethyl cellulose or hydroxypropyl cellulose. Such polymer matrix formulations are known to be useful in preparing compositions for various applications for human and animal use.

For example, a formulation containing sodium hyaluronate and hydroxyethylcellulose was formerly marketed under the name of Ionic Polymer Matrix (IPM) Wound Gel for applying to wounds to promote wound healing. In addition, polymer matrices of HA formulated with other active ingredients are known to be useful as topical drug formulations for delivering the active ingredients to sites below the dermal level of the skin. HA polymer matrix topical active ingredient formulations for trans-dermal delivery of active ingredients are disclosed for example in U.S. Pat. No. 5,897,880, U.S. Pat. No. 6,120,804, U.S. Pat. No. 6,387,407, and U.S. Pat. No. 6,723,345. HA polymer matrices formulated with other active ingredients are also known to be useful as formulations for sustained release of the pharmaceutical agents. HA polymer matrix formulations for sustained release delivery of active ingredients are disclosed in U.S. Pat. No. 6,063,405, U.S. Pat. No. 6,335,035, and U.S. Pat. No. 6,007,843.

Preparing sodium hyaluronate polymer matrix formulations presents many challenges. Initially, in the 1980s only HA obtained from animal sources was available commercially, and many of the formulations were delivered by injection, or used as drops in the eye, rather than for topical use for dermatological conditions. The natural HA used in various formulations has usually been obtained from rooster combs. The rooster comb (also known as a chicken comb) is an avian source and as such is of animal origin. As a result, sodium hyaluronate formulations manufactured using sodium hyaluronate from rooster combs have been known to cause allergies and carry other risks associated with products of animal origin, namely a risk of transmission of animal diseases to humans. Consequently, the currently approved topical products containing sodium hyaluronate formulations available on the market are contra-indicated for those patients who are hypersensitive to sodium hyaluronate of animal origin.

Moreover, sodium hyaluronate is difficult to formulate in high concentrations above 1.5% w/w, due to the difficulty in manufacturing a formulation that maintains stability and is not too viscous for normal use when packaged in a tube. For this reason many of the commercial formulations on the market have a concentration of HA or sodium hyaluronate well below 1% w/w, and many in fact have a concentration at around 0.2% w/w. To the inventors' knowledge, there are no products currently on the market that contain more than 1.5% w/w sodium hyaluronate. When not mixed and manufactured properly, a high HA or sodium hyaluronate concentration formulation will quickly break down, and therefore the percentage of HA or sodium hyaluronate in the formulation will fall below the acceptable limit (+/−10% of original amount), resulting in a very short shelf life for the product. Formulations containing a high concentration of sodium hyaluronate therefore present a challenge due to the instability of the matrix. This results in inconsistencies in the matrix formulation and impairs the ability of sodium hyaluronate formulations to perform their functions. For example, when applied to wounds to promote healing, a sodium hyaluronate polymer matrix formulation helps to maintain a moist wound environment, an effect that is dependent on the formulation maintaining its high level of sodium hyaluronate concentration. The maintenance of a moist wound environment is widely recognized to positively contribute to wound healing. However, due to their instability and the resulting drop in the level of sodium hyaluronate that occurs as the formulation breaks down, high concentration sodium hyaluronate formulations are not effective in maintaining a moist environment. When formulated for the delivery of a drug, the inconsistency of high concentration sodium hyaluronate formulations reduces the ability of such formulations to allow the drug to diffuse through the tissue when administered, thereby impairing their ability to achieve the therapeutic dose.

In addition, the sodium hyaluronate polymer matrix formulation product formerly marketed under the name of Ionic Polymer Matrix (IPM) Wound Gel was withdrawn from the market due to problems with the formulation.

Therefore, a need exists for a method for formulating a sodium hyaluronate polymer matrix containing a high concentration of sodium hyaluronate that can be manufactured and sold commercially.

SUMMARY OF THE INVENTION

The present invention relates to stable polymer matrix compositions, preferably pharmaceutical compositions, comprising a high concentration (for example, from about 1.5% to about 3.5% w/w) of sodium hyaluronate obtained from a bacterial source such as *Streptococcus zooepidemicus* or *Bacillus subtilis* source. Sodium hyaluronate obtained from a bacterial source is referred to hereinafter as "bio-fermented" sodium hyaluronate. The compositions further comprise a non-ionic polymer optionally in an amount of from about 0.1% to about 2% w/w, polyethylene glycol, methylparaben and water. By "stable", as used herein, it is meant that the amount of sodium hyaluronate in the formulation does not vary by more than +/−10% (w/w) relative to the original amount provided in the composition, at 40° C., 75% relative humidity (accelerated stability conditions) for a period of at least 6 months, and/or at 25° C., 60% relative humidity (long-term stability conditions) for a period of at least 18 months. The amount of sodium hyaluronate may be measured by HPLC techniques known in the art of pharmaceutical development.

In one aspect of the present invention, the polymer matrix compositions of the present invention comprise components which are of compendial (USP or Ph. Eur.) and/or of pharmaceutical grade. These terms are discussed further below. Preferably, all the components of the compositions are of compendial and/or of pharmaceutical grade. In a further aspect of the invention, the polymer matrix compositions comprise components of certain specifications.

In one aspect, polymer matrix compositions of the present invention may be used in the treatment of wounds, burns, and certain dermatological conditions.

In another aspect of the present invention, the polymer matrix compositions comprise an active ingredient. In this aspect of the invention, the polymer matrix compositions may be used for trans-dermal delivery, topical delivery, and sustained release delivery of the active ingredient.

In some aspects, the polymer matrix compositions may be used for the treatment of musculoskeletal pain. A further aspect of the present invention relates to the use of the polymer matrix compositions in the treatment of vaginal dryness.

In a further aspect, the present invention relates to methods for preparing stable polymer matrix compositions of the present invention.

DETAILED DESCRIPTION OF THE INVENTION

The inventors determined that the product IPM Wound Gel could not be successfully formulated because the product was made from naturally sourced sodium hyaluronate ("natural sodium hyaluronate") and because the testing regimen was not sufficient and raw materials were not of sufficient quality. The natural sodium hyaluronate was produced from rooster combs (which is an animal origin source) and was of cosmetic grade. The natural sodium hyaluronate was found to be more prone to microbiological contamination including that from the manufacturing facility and surrounding environment. This led to microbiological failure of the product rendering the product unsafe and not useful. Moreover, the product IPM Wound Gel used ingredients that were of insufficient or inconsistent grade. Also, testing to determine the quality of the IPM Wound Gel Product was insufficient to ensure a stable product of sufficient quality.

The inventors unexpectedly discovered that sodium hyaluronate polymer matrix compositions can be advantageously formulated using bio-fermented sodium hyaluronate obtained from strains of *Streptococcus zooepidemicus* or *Bacillus subtilis* bacteria.

The inventors further determined that sodium hyaluronate polymer matrix compositions can be advantageously formulated by using ingredients of sufficient quality, i.e., ingredients of compendial (USP or Ph. Eur.) and/or pharmaceutical grade, including bio-fermented sodium hyaluronate. An ingredient or component of pharmaceutical grade, as provided herein, may be defined as an ingredient or a component having at least 99% purity, preferably not containing binders, fillers, excipients, dyes, or unknown substances. In some embodiments, an ingredient of pharmaceutical grade additionally meets one or more of the following criteria: the ingredient has an endotoxin level of 0.5 EU/mg or less (or 0.5 EU/ml or less for liquid ingredients), the ingredient has a total aerobic microbial count (TAMC) of less than 100 cfu/g, (or less than 100 cfu/ml for liquid ingredients), the ingredient has a total yeast and mold count (TYMC) of less than 10 cfu/g (or less than 10 cfu/ml for liquid ingredients), the ingredient has a nucleic acid content of 0.5% w/w or less, and the ingredient has a protein content of 0.3% w/w or less. Methods of measuring endotoxin levels, TAMC, TYMC, nucleic acid levels and protein levels would be known to the person skilled in the art of pharmaceuticals. An ingredient or component of compendial grade refers to a grade of ingredient with full compendial testing as appropriate to the USP (US Pharmaceopeia), NF (National Formulary), BP (British Pharmacopeia) or Ph. Eur. (European Pharmacopeia), thus meeting chemical purity standards which are established by these recognized national or regional pharmacopeia authorities. Typically, an ingredient or component which is of compendial grade will also be of pharmaceutical grade. Validated assays methods for testing the amount of sodium hyaluronate and methylparaben in the formulations, as well as through compliance with Bacterial Endotoxin Test ("BET"), and microbiological test limits, including for *Staphylococcus aureus, Pseudomonas aeruginosa, Escherichia coli*, and *Salmonella* sp., as well as compliance with other parameters, have been used to confirm the quality of the formulations of the present invention. The present inventors have unexpectedly found that compositions according to the present invention have improved stability (i.e. the concentration of sodium hyaluronate in the formulation does not vary by more than +/−10% (w/w) relative to the original amount provided in the composition, at 40° C., 75% relative humidity (accelerated stability conditions) for a period of at least 6 months, and/or at 25° C., 60% relative humidity (long-term stability conditions) for a period of at least 18 months), improved wound-healing properties, and reduced cytotoxicity effects relative to comparable compositions comprising natural sodium hyaluronate which may be obtained from an avian source and non-pharmaceutical and/or non-compendial grade components (e.g. IPM Wound Gel). It is believed that the stability, wound-healing properties and cytotoxicity of the composition of the invention are improved with the use of bio-fermented sodium hyaluronate, and even further improved by the use of components which are of compendia' and/or pharmaceutical grade.

The inventors further developed a process for formulating a polymer matrix composition containing a high concentration (i.e., between about 1.5% w/w to about 3.5% w/w) of sodium hyaluronate and produced a stable polymer matrix composition containing a high concentration of sodium hyaluronate according to the present invention. Additionally, provided herein is a formulation obtained by the process.

In some embodiments, the process comprises the steps:
a) Adding methylparaben to water and mixing to produce a methylparaben solution,
b) Adding bio-fermented sodium hyaluronate to the methylparaben solution and mixing to produce a sodium hyaluronate solution,
c) Separately dissolving the non-ionic polymer, optionally hydroxycellulose, in water to produce a non-ionic polymer solution, d) Combining the sodium hyaluronate solution with the non-ionic polymer solution and mixing to produce a homogenous sodium hyaluronate non-ionic polymer solution, e) Adding polyethylene glycol to the sodium hyaluronate non-ionic polymer solution and mixing to form the polymer matrix composition.

Typically, the polymer matrix composition obtained by the method comprises from about 1.5% w/w/ to about 3.5% w/w bio-fermented sodium hyaluronate and from about 0.1% w/w to about 2.0% w/w non-ionic polymer, in addition to polyethylene glycol, methylparaben and water.

The method may further comprise a step of adding at least one active ingredient selected from: pantothenic acid, diclofenac sodium, niacin and glycerin.

Each of the components used in the process may be of compendial grade and/or pharmaceutical grade as defined herein. Preferably, all the components of the composition are of compendial grade and/or pharmaceutical grade. Each of the components may also be provided in the amounts defined herein and may have the properties (e.g. purity) defined herein.

Sodium hyaluronate (CAS Number: 9067-32-7, molecular formula $[C_{14}H_{20}N_{11}Na]_n$) consists of a linear polysaccharide, whose basic unit is a disaccharide of D-glucuronic acid and N-acetyl-D-glucosamine linked by a glucuronidic (1-3) bond. The disaccharides units are linearly polymerized by hexosaminidic (1-4) linkages, as shown in Formula 1:

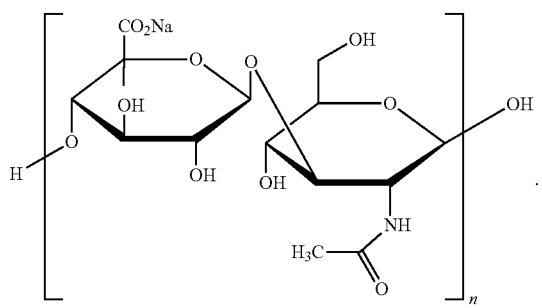

Sodium hyaluronate is a white or almost white, very hygroscopic powder or fibrous aggregate. It is odorless and the pH of the 5% solution is in the range of 5.0-8.5. Sodium hyaluronate is easily soluble in cold water and insoluble in organic solvents. Sodium hyaluronate of high quality, i.e., BET≤0.5 EU/g microbial quality, may be obtained from commercial suppliers.

The process of obtaining bio-fermented sodium hyaluronate can vary, but in general, the preparation involves the following steps: fermenting selected *Streptococcus zooepidemicus* bacterial strains; selecting the sodium hyaluronate crude product obtained from fermentation; purifying the crude product by filtration; precipitating sodium hyaluronate with an organic solvent; and drying. Bio-fermented sodium hyaluronate obtained from *Streptococcus zoopidemicus* is available commercially from suppliers such as QUFU, Freda, and Contipro.

As an example, U.S. Pat. No. 4,517,295 to Bracke et al. discloses the preparation of hyaluronic acid in high yield from *Streptococcus* bacteria by fermenting the bacteria under anaerobic conditions in a $CO_2$ enriched growth medium, separating the bacteria from the resulting broth and isolating the hyaluronic acid from the remaining constituents of the broth. Separation of the microorganisms from the hyaluronic acid is facilitated by killing the bacteria with trichloroacetic acid. After the removal of the bacteria cells and concentration of the higher molecular weight fermentation products, the hyaluronic acid is isolated and purified by precipitation, re-suspension and re-precipitation.

One particular fraction of bio-fermented sodium hyaluronate that exhibits excellent matrix formation according to the present invention is sodium hyaluronate having an average molecular weight between about 600,000 Daltons to about 800,000 Daltons. Bio-fermented sodium hyaluronate having an average molecular weight of 500,000 to 1,000,000 Daltons has also been found to be acceptable in the formulations of the present invention.

In addition to bio-fermented sodium hyaluronate, polymer matrix formulations of the present invention include a non-ionic polymer. Non-ionic polymers suitable for use in formulations of the present invention include polyvinylpyrrolidones, poloxamers, copovidone, polyvinyl alcohol, cellulose derivatives, sorbitol based polymers, locus bean gum, guar gum, maltodextrin, vinyl pyrrolidone copolymers, polyacrylamides, polyethylene oxide copolymers, neutralized polyacrylic acids, polysorbates, ethoxylates, polyalcohols, polyethylene glycol, methoxy methoxypolyethylene glycol (MPEG) and alpha, omega-dialkyl-ethoxylates, or mixtures thereof.

Polyvinylpyrrolidones suitable for use with the present invention include PVP K-90, PVP K-17, and polyvinyl pyrrolidone-vinyl acetate (PVP-VA) copolymer.

Cellulose derivatives suitable for use with the present invention include hydroxyethylcellulose, hydroxypropylmethylcellulose, ethyl(hydroxyethyl)cellulose, and methyl cellulose.

Sorbitol based polymers suitable for use with the present invention include Neosorb.

Polyacrylic acids suitable for use with the present invention include, but not limited to neutralized Carbopol 980, Carbopol 940 and Carbomer 981 (Old type Carbomer 941).

Polysorbates suitable for use with the present invention include Polysorbate 20 (USP/Ph. Eur.), Polysorbate 21, Polysorbate 40 (USP/Ph. Eur.), Polysorbate 60 (USP/Ph. Eur.), Polysorbate 61, Polysorbate 65, Polysorbate 80 (USP/Ph. Eur.), Polysorbate 81, Polysorbate 85, and Polysorbate 120.

Hydroxyethylcellulose ("HEC") is a particularly preferred non-ionic polymer for use with the present invention.

It is believed that there are many such non-ionic polymers that can be used to successfully form the polymer matrix formulations of the present invention. As such, included in the present invention are any non-ionic polymers that can successfully form a polymer matrix with sodium hyaluronate.

Other suitable ingredients for use in the manufacture of the polymer matrix compositions of the present invention include stabilizers and fillers such as methylparaben, benzyl alcohol, polyethylene glycol, methoxypolyethylene glycol, and purified water. Preferably, ingredients used in the bio-fermented sodium hyaluronate polymer matrix compositions of the present invention conform to the compendial standards (USP or Ph. Eur.)

In a preferred embodiment, the bio-fermented sodium hyaluronate used in the compositions of the present invention is of compendial or pharmaceutical grade quality. More preferably, all raw materials used in the formulations of the present invention are of high microbiological quality (i.e. of compendial and/or pharmaceutical grade). In contrast, in the IPM Wound Gel comprising sodium hyaluronate of animal origin, the individual components do not meet the compendial and/or pharmaceutical grade standards. The following Table 1 compares the changes made in specifications of raw materials from the formulation used in the product IPM Wound Gel to the formulation of the present invention.

TABLE 1

Changes to specifications of raw materials used in the formulation of the present invention in comparison to those used in the product IPM Wound Gel.

| IPM Wound Gel | Sodium hyaluronate bio-fermented formulation of the present invention |
|---|---|
| Sodium hyaluronate | |
| Grade: Cosmetic grade | Grade: Pharmaceutical grade (Ph. Eur.) |
| | Nucleic acid: ≤0.5% (Ph. Eur.) |
| Protein content ≤5% | Protein content ≤0.3% (Ph. Eur.) |
| TYMC ≤50 cfu (colony forming units)/g | TYMC ≤10 cfu/g (Ph. Eur.) |
| E. coli: Negative | Staphylococcus aureus: Absence (Ph. Eur.) |
| | Pseudomonas aeruginosa: Absence (Ph. Eur.) |
| | Escherichia coli: Absence (Ph. Eur.) |
| | Salmonella sp.: Absence (Ph. Eur.) |
| | Bacterial Endotoxin Test (BET) ≤0.5 IU/mg |
| Hydroxyethylcellulose (HEC) | |
| TAMC (Total Aerobic Microbial Count) <1000 cfu/g | TAMC <100 cfu/g (USP/Ph. Eur.) |
| Polyethylene Glycol 200 (PEG 200) | |
| PEG 200 or PEG 400 | PEG 200 |
| | Limit of ethylene glycol and diethylene glycol (combined): ≤0.25% w/w (USP) |
| | TAMC <100 cfu/mL (USP) |
| — | TYMC ≤10 cfu/mL (USP) |
| Methylparaben | |
| | TAMC <100 cfu/mL (USP/Ph. Eur.) |
| | TYMC ≤10 cfu/mL (USP/Ph. Eur.) |
| Purified water | |
| | TAMC <100 cfu/mL (USP/Ph. Eur.) |
| | BET <0.25 EU/mL (USP/Ph. Eur.) |

The grade of PEG used with IPM Wound Gel was intermittently PEG 400 which may have reduced the stability of the product. The matrix formed was less stable than the formulation of the present invention. The PEG used with the preferred embodiment of formulations of the present invention is of better purity in that the restricted substances, namely, ethylene glycol and diethylene glycol are well controlled.

Optionally, the PEG used in formulations of the present invention and specifically, in the methods of preparing the formulations, comprises ethylene glycol and diethylene glycol in a combined amount of less than 0.25% w/w. Preferably, the average molecular weight (mass average and/or number average) of the PEG used in formulations of the present invention and in the methods of preparing the compositions, is 200 Da. (This is referred to hereinafter as "PEG 200 grade".) In some embodiments, the average molecular weight (mass average and/or number average) of the PEG is not less than 190 or more than 210. In some embodiments, the amount of PEG having a molecular weight of at least 400 Da is less than 5, 4, 3, 2 or 1 weight % by total weight of the PEG. In some embodiments, the PEG is present in the formulations in an amount of from about 0.5% to about 10% w/w, or from about 1% to about 5% w/w, or from about 2% to about 4% w/w, or about 3% w/w.

Sodium hyaluronate used with the IPM Wound Gel was of cosmetic grade and did not meet compendial and/or pharmaceutical grade requirements as defined herein. In the preferred embodiment, the present invention uses sodium hyaluronate of pharmaceutical grade and/or compendial grade with consistent quality. Preferably, the sodium hyaluronate has a low content of nucleic acid and protein (e.g. a nucleic acid content of 0.5% w/w/ or less and/or a protein content of 0.3% w/w or less). In the preferred embodiment of the present invention, the TYMC microbial count is better controlled (e.g. 10 cfu/g or less), and all the specified microorganisms are tested for their absence. Additionally, in the preferred embodiment of the present invention, BET is tested and is 0.5 EU/mg or less, and the protein content of sodium hyaluronate has been significantly reduced (e.g. from 5% w/w or less for IPM Wound Gel to 0.3% w/w or less for the preferred embodiment of the present invention).

In regard to HEC used in the preferred embodiment of the present invention, there is a better control of microbial count (e.g. the HEC has a TAMC of less than 100 cfu/g) than with the HEC used with IPM Wound Gel (e.g. the HEC has a TAMC of less than <1000 cfu/g) provided by the raw material supplier. Hence the formulation of the present invention in the preferred embodiment was found to be significantly better quality.

In the preferred embodiment of the present invention, methylparaben raw material is tested for TAMC and TYMC tests to ensure that only good quality raw material is used in the manufacture of the formulation in the preferred embodiment of the present invention. For example, the TAMC and TYMC of the methylparaben is preferably 10 cfu/ml or less. The methylparaben may be present in the formulations of the present invention in an amount of from about from about 0.01 to about 0.3% w/w, from about 0.1 to about 0.3% w/w or about 0.2% w/w.

Additionally, in the preferred embodiment of the present invention, purified water is better controlled microbiologically by performing additional tests TAMC and BET. For example, the TAMC of water is 100 cfu/ml or less, and/or the BET of water is 0.25 EU/ml or less.

The bio-fermented sodium hyaluronate polymer matrix formulation is a clear viscous, odorless, aqueous gel composed principally of sodium hyaluronate, a derivative salt of hyaluronic acid. The formulation of bio-fermented sodium hyaluronate is a polymer matrix made up of negatively charged polymer, namely, sodium hyaluronate, and a non-ionic polymer, such as HEC. In other words, sodium hyaluronate (as a negatively charged polymer) forms part of the polymer matrix in combination with a non-ionic polymer, such as HEC, and it helps to maintain the moist environment through the matrix.

The concentration of sodium hyaluronate in the polymer matrix is from about 1.5% to about 3.5% w/w, or from about 2% to about 3% w/w, or from about 2.3% to 2.7% w/w, or about 2.5% w/w. The concentration of the non-ionic polymer, other than HEC, is from about 0.1% w/w to about 2.0% w/w, preferably from about 0.5% to 1.5% w/w, and more preferably, from about 0.7% w/w to about 1.3% w/w. In some embodiments, the non-ionic polymer is present in an amount of about 1% w/w. The concentration of HEC may be from about 0.1% w/w to about 2.0% w/w, or from about 0.1% w/w to about 1.5% w/w, preferably from about 0.5% to 1.5% w/w, and more preferably, from about 0.7% w/w to about 1.3% w/w.

Preferably, non-ionic polymers such as HEC are of compendial or pharmaceutical grade, as defined above. Where non-ionic polymers are not available in compendial or pharmaceutical grade, non-ionic polymers of best available quality should be used.

The viscosity of bio-fermented sodium hyaluronate polymer matrix formulation should be in the acceptable limits or range so that the matrix is stable and is easy to apply on the skin, wound, or other tissue. The formulation should also have a viscosity that can be handled easily during manufacturing and filling. The viscosity range has been investigated. It was determined that the formulation of the present invention should have a viscosity of about 10,000 to 50,000 cps (cP) when tested at room temperature (23° C., 77° F.). The therapeutically useful pH range of the formulation was set at 5.0 to 7.0.

In a preferred embodiment, the polymer matrix composition of the present invention may comprise bio-fermented sodium hyaluronate in an amount of from about 2.3 to about 2.7% w/w, non-ionic polymer, preferably hydroxycellulose, in an amount of from about 0.5 to about 1.5% w/w, polyethylene glycol in an amount of from about 1 to about 4% w/w, and methylparaben in an amount of from about 0.1 to about 0.3% w/w.

Most preferably, the bio-fermented sodium hyaluronate polymer matrix formulation comprises sodium hyaluronate (2.5%, w/w), HEC (1% w/w), methylparaben (0.2% w/w), polyethylene glycol (3%, w/w) and purified water, USP (approx. 93%, w/w). In preferred embodiments, all the components/ingredients are of compendial grade and/or pharmaceutical grade as defined herein. The test results found that in a particular embodiment, the average viscosity of this bio-fermented sodium hyaluronate formulation is 30,000 cps, i.e. exactly in the middle of the range (10,000-50,000 cps), at room temperature. It is well known that molecular weight of sodium hyaluronate and concentration of sodium hyaluronate have a direct effect on the viscosity of the product.

The solutions used to prepare the gels of the present invention may be prepared in a variety of ways. The non-ionic polymer such as HEC may be dissolved in water, mixed with anionic or negatively charged sodium hyaluronate solution to form the sodium hyaluronate/non-ionic polymer matrix, and then the optional active ingredient may be added or loaded to the system.

The preparation procedure may involve dissolving a non-ionic polymer such as HEC in water at a low speed (from about 25 rpm to less than about 400 rpm) to medium speed (from about 400 rpm to less than about 2000 rpm) for a few hours (about 1 to about 2 hours).

Separately, sodium hyaluronate may be slowly added to water while stirring at high speed, followed by stirring at medium speed (from about 400 rpm to less than about 2000 rpm) for a few hours (about 2 hours), followed by stirring at low speed from about 25 rpm to less than about 400 rpm for a long duration (overnight, or about 8 hours to about 15 hours) until all of the sodium hyaluronate polymer has dissolved into the mixture and a crystal-clear viscous solution has formed.

The non-ionic polymer such as HEC solution may be added to the sodium hyaluronate solution and mixed at medium speed (from about 400 rpm to less than about 2000 rpm) followed by mixing at low to medium speed (from about 25 rpm to less than about 2000 rpm) for a long period (from about 4 hours to about 15 hours) until a homogenous solution is produced.

Conventional pharmaceutically acceptable emulsifiers, suspending agents, solvents (such as polyethylene glycol 200), antioxidants (such as sodium meta-bisulfate) and preservatives (such as benzyl alcohol, methylparaben) may then be added to this system.

When formulated with an active ingredient as a system for transdermal or sustained release of the active ingredient, using safe techniques, the active ingredient (e.g., 3% diclofenac sodium) may be slowly added to the above sodium hyaluronate/non-ionic polymer matrix mixture while increasing the speed to high speed (from about 2000 rpm to about 3000 rpm), and the addition of the entire quantity of the active ingredient should be completed within a short duration (about 15 minutes).

Once all the components are blended together, such as by mixing at low speed (from about 25 rpm to less than about 400 rpm) to medium speed (from about 400 rpm to less than about 2000 rpm) for about 2 hours to about 20 hours, the system is filled into tubes. The resulting system is clear to slightly hazy, colourless, viscous, odorless gel which are found to be stable on storage for a few years (from 18 months to 4 years).

Preferably, a bio-fermented sodium hyaluronate polymer matrix formulation according to the invention is prepared as follows. First, add methylparaben to water in a suitable container and mix at medium speed (from about 400 rpm to less than about 2000 rpm) for few hours (about 2 hours). Ensure that methylparaben is completely dissolved. Then slowly add sodium hyaluronate in a steady flow to the mixture gradually increasing the stirring speed from medium speed (from about 400 rpm to less than about 2000 rpm) to high speed (from about 2000 rpm to less than about 3000 rpm) as the mixture thickens and the spin stays while charging sodium hyaluronate in a suitable container (for about 1 hour). Mix for few hours (about 2 hours) at medium speed (from about 400 rpm to less than about 2000 rpm). Continue the mixing at low speed (from about 25 rpm to less than about 400 rpm) for long duration (about 8 hours) until all of the sodium hyaluronate polymer has dissolved into the mixture and a crystal-clear viscous solution has formed.

In a separate container dissolve the HEC (e.g. 1%) in purified water while stirring at medium speed (from about 400 rpm to less than about 2000 rpm) and mix well. Continue stirring for a few hours (from about 1 to about 2 hours).

The resulting HEC solution is added to the sodium hyaluronate solution and mixed at medium speed (from about 400 rpm to less than about 2000 rpm) followed by low speed (from about 25 rpm to less than about 400 rpm) for a long period (about 4 hours) until a homogenous solution is produced.

Add polyethylene glycol into the mixture while mixing at a medium speed (from about 400 rpm to less than about 2000 rpm). Continue mixing at medium speed for about 1 hour. Reduce the speed and continue mixing at low speed (from about 25 rpm to less than about 400 rpm) for a few hours (minimum of about 3 hours). The bulk gel may then be filled in tubes or bottles and capped.

Further provided is a polymer matrix composition obtained by this method.

In some embodiments, the formulations of the invention as defined herein further comprise an active ingredient. Thus, the methods of preparing the formulations defined herein may comprise a further step of adding an active ingredient.

For example, specifically provided is a stable polymer matrix composition comprising 1.5% w/w bio-fermented sodium hyaluronate, 1.0% w/w hydroxyethylcellulose, 3.0% w/w polyethylene glycol, 0.2% w/w methylparaben, 1.5% w/w pantothenic acid, and water. Preferably, each component is of compendial grade and/or of pharmaceutical grade. More preferably, the bio-fermented sodium hyaluronate is of pharmaceutical grade according to the European Pharmacopoeia, has nucleic acid content of less than or equal to 0.5%, has protein content of less than or equal to 0.3%, TYMC of less than or equal to 10 cfu/g, BET score of less than or equal to 0.5 IU/mg, and tests absent for *Staphylococcus aureus, Pseudomonas aeruginosa, Escherichia coli*, and *Salmonella* sp.; the hydroxyethylcellulose has a TAMC of less than 100 cfu/g; the polyethylene glycol is of PEG 200 grade and has a combined ethylene glycol and diethylene glycol content of less than or equal to 0.25%, TAMC of less than 100 cfu/mL and TYMC of less than or equal to 10 cfu/mL; the methylparaben has a TAMC of less than 100 cfu/mL and TYMC of less than or equal to 10 cfu/mL; and the water is purified having a TAMC of less than 100 cfu/mL and a BET score of less than 0.25 EU/mL.

A method of making such a composition comprises the steps:
Adding methylparaben to water and mixing at medium speed for about 2 hours until completely dissolved to produce a methylparaben solution;
Adding bio-fermented sodium hyaluronate to the methylparaben solution in a steady flow gradually increasing the stirring speed from medium to high as the mixture thickens and the spin stays while charging sodium hyaluronate;
Mixing for about 2 hours at medium speed followed by mixing at low speed about 8 hours to 15 hours;
Separately, dissolving hydroxyethylcellulose in water while stirring at medium speed and mixing well;
Stirring the hydroxyethylcellulose mixture for about 1 to about 2 hours to produce a hydroxyethylcellulose solution;
Adding the hydroxyethylcellulose solution to the sodium hyaluronate solution;
Mixing at medium speed until a homogenous solution is produced, followed by mixing at medium speed about 8 hours to 15 hours;
Adding polyethylene glycol into the sodium hyaluronate hydroxyethylcellulose solution while mixing at a medium speed for about 1 hour; and
Adding pantothenic acid and mixing well at medium speed for about 2 hours until dissolved and the gel is homogenous. "Low", "medium" and "high" speeds are as defined above. Further provided is a polymer matrix composition obtained by this method.

The stable polymer matrix composition comprising 1.5% w/w bio-fermented sodium hyaluronate, 1.0% w/w hydroxyethylcellulose, 3.0% w/w polyethylene glycol, 0.2% w/w methylparaben, 1.5% w/w pantothenic acid, and water as defined herein or obtained by the method described herein may be used in the treatment for damaged skin and/or in the treatment of atopic dermatitis.

Further provided is a stable polymer matrix composition comprising: 2.3% w/w bio-fermented sodium hyaluronate, 0.7% w/w hydroxyethylcellulose, 10% w/w methoxypolyethylene glycol, 0.3% w/w methylparaben, 3.0% w/w diclofenac sodium, and water. Preferably, each component is of compendial grade or pharmaceutical grade. More preferably, the bio-fermented sodium hyaluronate is of pharmaceutical grade according to the European Pharmacopoeia, has nucleic acid content of less than or equal to 0.5%, has protein content of less than or equal to 0.3%, TYMC of less than or equal to 10 cfu/g, BET score of less than or equal to 0.5 IU/mg, and tests absent for *Staphylococcus aureus, Pseudomonas aeruginosa, Escherichia coli*, and *Salmonella* sp.; the hydroxyethylcellulose has a TAMC of less than 100 cfu/g; the methoxypolyethylene glycol is of USP compedial grade; the methylparaben has a TAMC of less than 100 cfu/mL and TYMC of less than or equal to 10 cfu/mL; and the water is purified having a TAMC of less than 100 cfu/mL and a BET score of less than 0.25 EU/mL.

A method of making such a composition comprises the steps:
Adding methylparaben to water and mixing at medium speed for about 2 hours until completely dissolved to produce a methylparaben solution;
Adding bio-fermented sodium hyaluronate to the methylparaben solution in a steady flow gradually increasing the stirring speed from medium to high as the mixture thickens and the spin stays while charging sodium hyaluronate;
Mixing for about 2 hours at medium speed followed by mixing at low speed for about 8 hours until all of the sodium hyaluronate has dissolved to produce a sodium hyaluronate solution;
Separately, dissolving hydroxyethylcellulose in water while stirring at low to medium speed and mixing well;
Stirring the hydroxyethylcellulose mixture for about 1 to 2 hours to produce a hydroxyethylcellulose solution;
Adding the hydroxyethylcellulose solution to the sodium hyaluronate solution;
Mixing at medium speed for about 10 to about 15 hours until a homogenous solution is produced;
Adding methoxypolyethylene glycol into the sodium hyaluronate hydroxyethylcellulose solution while mixing at a high speed;
Mixing at medium speed for about 3 to about 4 hours; and
Over a period of about 15 minutes, slowly adding diclofenac sodium while mixing at high speed; and
Mixing at medium speed for about 15 to 20 hours. "Low", "medium" and "high" speeds are as defined above. Further provided is a polymer matrix composition obtained by this method.

The stable polymer matrix composition comprising: 2.3% w/w bio-fermented sodium hyaluronate, 0.7% w/w hydroxyethylcellulose, 10% w/w methoxypolyethylene glycol, 0.3% w/w methylparaben, 3.0% w/w diclofenac sodium, and water as defined herein or obtained by the method defined herein, may be used to treat actinic keratosis and/or to treat musculoskeletal pain.

Further provided is a stable polymer matrix composition comprising: 1.5% w/w bio-fermented sodium hyaluronate, 0.7% w/w hydroxyethylcellulose, 3% w/w polyethylene glycol, 0.2% w/w methylparaben, 0.85% w/w niacin, 3% w/w glycerin, and water. Preferably, each component is of compendial grade or pharmaceutical grade. More preferably, the bio-fermented sodium hyaluronate is of pharmaceutical grade according to the European Pharmacopoeia, has nucleic acid content of less than or equal to 0.5%, has protein content of less than or equal to 0.3%, TYMC of less than or equal to 10 cfu/g, BET score of less than or equal to 0.5 IU/mg, and tests absent for *Staphylococcus aureus, Pseudomonas aeruginosa, Escherichia coli*, and *Salmonella* sp., the hydroxyethylcellulose has a TAMC of less than 100 cfu/g; the polyethylene glycol is of PEG 200 grade and has a combined ethylene glycol and diethylene glycol content of less than or equal to 0.25%, TAMC of less than 100 cfu/mL and TYMC of less than or equal to 10 cfu/mL; the methylparaben has a TAMC of less than 100 cfu/mL and TYMC of less than or equal to 10 cfu/mL; the water is purified having a TAMC of less than 100 cfu/mL and a BET score of less than 0.25 EU/mL.

A method of making such a composition comprises the steps:

Adding methylparaben to water and mixing at medium speed for about 2 hours until completely dissolved to produce a methylparaben solution;

Slowly adding bio-fennented sodium hyaluronate to the methylparaben solution in a steady flow while gradually increasing the stirring speed from medium to high as the mixture thickens and the spin stays while charging sodium hyaluronate;

Mixing for about 2 hours at medium speed following by mixing at low speed about 8 hours to 15 hours until all of the sodium hyaluronate has dissolved to produce a sodium hyaluronate solution;

Separately, dissolving hydroxyethylcellulose in water while stirring at low to medium speed and mixing well;

Stirring the hydroxyethylcellulose mixture for about 1 to about 2 hours to produce a hydroxyethylcellulose solution;

Adding the hydroxyethylcellulose solution to the sodium hyaluronate solution;

Mixing at medium speed about 8 hours to 15 hours to produce a homogenous sodium hyaluronate hydroxyethylcellulose solution;

Adding polyethylene glycol into the sodium hyaluronate hydroxyethylcellulose solution;

Mixing at medium speed for about 2.5 hours;

Adding niacin and glycerin; and

Stirring at low speed for about 2 hours. "Low", "medium" and "high" speeds are as defined above. Further provided is a polymer matrix composition obtained by this method.

The stable polymer matrix composition comprising 1.5% w/w bio-fermented sodium hyaluronate, 0.7% w/w hydroxyethylcellulose, 3% w/w polyethylene glycol, 0.2% w/w methylparaben, 0.85% w/w niacin, 3% w/w glycerin, and water, as defined herein or obtained by the method defined above may be used in the in the treatment of vaginal dryness.

The polymer matrix compositions formulated with bio-fermented sodium hyaluronate of the present invention can be used in the manufacture of pharmaceutical compositions, medical device compositions, natural health product compositions, and dietary supplement compositions. In topical applications, the polymer matrix compositions of the present invention serve to maintain moist wound environment. The maintenance of a moist wound environment is widely recognized to positively contribute to wound healing process and relief from certain dermatological conditions. The polymer matrix compositions formulated with bio-fermented sodium hyaluronate of the present invention may be used for topical applications or transdermal applications. For example, the polymer matrix compositions formulated with bio-fermented sodium hyaluronate of the present invention may be used for topical application in the treatment of many types of ulcers (wounds), including venous stasis, diabetic wounds and diabetic ulcers, and post-operative incisions, and in anti-aging treatments. The invention has shown to be especially effective in hard-to-heal wounds. In particular, the compositions of the present invention are effective in promoting the healing of surgical incisions in diabetic patients. For example, the compositions of the present invention are effective in promoting the healing of surgical incisions in diabetic patients following digit amputations, particularly in diabetic patients suffering from osteomyelitis.

More particularly, the polymer matrix compositions formulated in with bio-fermented hyaluronate of the present invention have been shown to be useful in topical applications for the management/treatment of dermatological conditions, burns ($1^{st}$ degree burns), minor abrasions, minor cuts, and in helping to relieve dry waxy skin irritations association with dry skin conditions. Furthermore, the polymer matrix compositions formulated in with bio-fermented hyaluronate of the present invention have been shown be useful in topical applications for the management of exudating wounds such as leg ulcers, pressure ulcers, diabetic ulcers, surgical wounds (post-operative and donor sites), mechanically or surgically debrided wounds, second degree burns, and the management and relief of burning, itching and pain associated with various types of dermatoses, including atopic dermatitis, allergic contact dermatitis, and radio-dermatitis.

In other aspects, the polymer matrix compositions formulated with bio-fermented sodium hyaluronate of the present invention may be also used in the manufacture of a system for a sustained release delivery of an active ingredient, and in the manufacture of a system for topical application, topical delivery or transdermal delivery of an active ingredient.

In additional aspects, the polymer matrix compositions formulated with bio-fermented sodium hyaluronate of the present invention can be used in the manufacture of personal lubricants for use in the management of symptoms of female sexual dysfunction.

When formulated with an active ingredient as a system for transdermal delivery of an active ingredient, the bio-formulated sodium hyaluronate polymer matrix formulation is believed to form a matrix which microencapsulates, suspends, and/or entraps the active ingredient such that when it is administered, it is slowly released into the systemic circulatory system or muscular tissue providing a method of delivering an active ingredient to an affected site in the body through the skin.

The active ingredient may be added either directly to the homogenous solution or gel of sodium hyaluronate and a non-ionic polymer such as HEC or it may be separately dissolved or disbursed in water before addition to the homogenous solution or gel of sodium hyaluronate and a non-ionic polymer such as HEC and mixed well. The active ingredient must be solubilized in the polymer matrix solution in order to be topically administered. Conventional pharmaceutically acceptable excipients well known to those skilled in the art, such as surfactants, suspending agents, emulsifiers osmotic enhancers, extenders and dilutants, pH modifiers as well as fragrances, colors, flavors and other additives may be added to this system. One particularly non-limiting effective material for solubilizing water insoluble drugs is methoxypolyethylene glycol (MPEG). Once all the components are blended together, for medium speed for 1 to 4 hours, the system is filled into tubes or bottles, sterilized, if required, and stored for future use.

The formulations of this invention formulated with an active ingredient for topical application, or for topical delivery of an active ingredient or trans-dermal delivery of an active ingredient may potentially be used to treat a variety of mammal and animal conditions and physical states. These systems may have a particular application to pain management, namely the treatment and alleviation of pain associated with any disease, condition or physical state.

Without being limited to the specific pain being treated, the preparations of this invention formulated with an active ingredient for topical application/delivery or for transdermal delivery may treat the following non-limiting locations or sources of pain below the dermal level of the skin, including, but not limited to knees, ankles, hands, feet and neck.

In addition to treating disorders associated with pain below the dermal level of the skin, the preparations of this invention formulated with an active ingredient for topical application/delivery or for transdermal delivery may be used to treat a wide variety of dermatologic disorders as well as many types of ulcers (wounds) including venous stasis and diabetic wounds. The invention has shown to be especially effective in hard to heal wounds. Exemplary, non-limiting disorders that may potentially be treated with the preparations of this invention formulated with an active ingredient for topical application or transdermal delivery include dermatitis conditions such as: Contact Dermatitis; Atopic Dermatitis; Radio Dermatitis; Seborrheic Dermatitis; Nummular Dermatitis; Chronic Dermatitis of Hands and Feet; Generalized Exfoliative Dermatitis; Stasis Dermatitis; and Localized Scratch Dermatitis; bacterial infections of the skin, such as: Staphylococcal Diseases of the Skin, Staphylococcal Scalded Skin Syndrome; Erysipelas; Folliculitis; Furuncles; Carbuncles; Hidradenitis Suppurativa; Paronychial Infections and Erythrasma; superficial fungal infections such as: Dermatophyte Infections; Yeast Infections; Candidiasis; and Tinea Versicolor; parasitic infections of the skin such as: Scabies; Pediculosis; and Creeping Eruption; disorders of hair follicles and sebaceous glands such as: Acne; Rosacea; Perioral Dermatitis; Hypertrichosis; Alopecia; Pseudofolliculitis Barbae; and Keratinous Cyst; scaling papular diseases, such as: Psoriasis; Pityriasis Rosea; and Lichen Planus; pressure sores; benign tumors and malignant tumors.

A wide variety of active ingredients which may be administered topically may be used in the topical or transdermal delivery system according to this invention. These may include drugs from all major categories, and without limitation, for example, anesthetics including benzocaine, tetracaine, mepivacaine, prilocaine, etidocaine, bupivacaine and lidocaine; analgesics, such as acetaminophen, ibuprofen, fluriprofen, ketoprofen, voltaren (U.S. Pat. No. 3,652,762), phenacetin and salicylamide; nonsteroidal anti-inflammatories (NSAIDS) selected from the group consisting of naproxen, acetaminophen, ibuprofen, flurbiprofen, ketoprofen, phenacetin, salicylamide, and indomethacin; antibiotics including amebicides, broad and medium spectrum, fungal medications, monobactams and viral agents and specifically including such as erythromycin, penicillin and cephalosporins and their derivatives; central nervous system drugs such as thioridazine, diazepam, meclizine, ergoloid mesylates, chlorpromazine, carbidopa and levodopa; metal salts such as potassium chloride and lithium carbonate; minerals selected from the group consisting of iron, chromium, molybdenum and potassium; immunomodulators; immunosuppressives; thyroid preparations such as synthetic thyroid hormone, and thyroxine sodium; steroids and hormones including ACTH, anabolics, androgen and estrogen combinations, androgens, corticoids and analgesics, estrogens, glucocorticoid, gonadotropin, gonadotropin releasing, human growth hormone, hypocalcemic, menotropins, parathyroid, progesterone, progestogen, progestogen and estrogen combinations, somatostatis-like compounds, urofollitropin, vasopressin, and others; and vitamins selected from water-soluble vitamins such as B complex including vitamin B5 and B3 (Niacin), vitamin C, vitamin B12 and folic acid and veterinary formulations.

Doses may vary from patient to patient depending on the type and severity of the condition being treated and the active ingredient being administered. Generally, doses of 1 ml to 75 ml may be administered with preferred doses using 2 to 25 ml of the gelled matrix system.

When formulated with another active ingredient as a system for sustained release of an active ingredient, the bio-formulated sodium hyaluronate polymer matrix formulation may allow an effective therapeutic level of an active ingredient to be administered once over at least a 24 hour to several day interval. It is believed that the bio-formulated sodium hyaluronate polymer matrix formulation forms a matrix which microencapsulates, suspends and/or entraps the active ingredient such that when it is administered it is slowly released into the systemic circulatory system or muscular tissue providing a sustained and prolonged active ingredient release rate.

A wide variety of active ingredients may be used in the sustained delivery system according to this invention. These may include drugs from all major categories, and without limitation, for example, anesthetics including those used in caudal, epidural, inhalation, injectable, retrobulbar, and spinal applications, such as bupivacaine and lidocaine; analgesics, such as acetaminophen, ibuprofen, fluriprofen, ketoprofen, voltaren (U.S. Pat. No. 3,652,762), phenacetin and salicylamide; anti-inflammatories selected from the group consisting of naproxen and indomethacin; antihistamines, such as chlorpheniramine maleate, phenindamine tartrate, pyrilamine maleate, doxylamine succinate, phenyltoloxamine citrate, diphenhydramine hydrochloride, promethazine, brompheniramine maleate, dexbrompheniramine maleate, clemastine fumarate and triprolidine; antitussive selected from the group consisting of dextromethorphan hydrobromide and guaifenesin; expectorants such as guaifenesin; decongestants, such as phenylephrine hydrochloride, phenylpropanolamine hydrochloride, pseudoephedrine hydrochloride, ephedrine; antibiotics including amebicides, broad and medium spectrum, fungal medications, monobactams and viral agents and specifically including such as erythromycin, penicillin and cephalosporins and their derivatives; bronchodilators such as theophylline, albuterol and terbutaline; cardiovascular preparations such as diltiazem, propranolol, nifedepine and clonidine including alpha adrenocepro agonist, alpha receptor blocking agent, alpha and beta receptor blocking agent, angiotensin converting enzyme inhibitors, beta blocking agents, calcium channel blocker, and cardiac glycosides; central nervous system drugs such as thioridazine, diazepam, meclizine, ergoloid mesylates, chlorpromazine, carbidopa and levodopa; metal salts such as potassium chloride and lithium carbonate; minerals selected from the group consisting of iron, chromium, molybdenum and potassium; immunomodulators; immunosuppressives; thyroid preparations such as synthetic thyroid hormone, and thyroxine sodium; steroids and hormones including ACTH, anabolics, androgen and estrogen combinations, androgens, corticoids and analgesics, estrogens, glucocorticoid, gonadotropin, gonadotropin releasing, human growth hormone, hypocalcemic, menotropins, parathyroid, progesterone, progestogen, progestogen and estrogen combinations, somatostatin-like compounds, urofollitropin, vasopressin, and others; and vitamins selected from water-soluble vitamins such as B complex, vitamin C, vitamin B12 and folic acid and veterinary formulations. Dosage forms may also involve the use of bupivacaine, lidocaine, vitamin B12, methyl prednisolone and adenosine-5-monophosphate sodium.

The active ingredient may be added directly to the homogenous solution or gel of sodium hyaluronate and a non-ionic polymer such as HEC or else it may be separately dissolved or disbursed in water before addition to the homogenous solution or gel of sodium hyaluronate and a non-ionic polymer such as HEC. Conventional pharmaceutically acceptable excipients well known to those skilled in the art, such as surfactants, suspending agents, emulsifiers osmotic enhancers, extenders and dilutants, pH modifiers as well as fragrances, colors, flavors and other additives may be added to this system. Once all the components are blended together, for medium speed for 1 to 4 hours, the system is filled into tubes or bottles, sterilized, and stored for future use.

The dosage form of this invention, in solution or suspension form, may be used topically or by injection intramuscularly, epidurally or subcutaneously. Dosages may vary from patient to patient depending on the type and severity of the condition being treated and drug being administered. The active ingredient must be solubilized in the polymer matrix solution in order to be topically administered.

The formulations of this invention formulated with an active ingredient for sustained delivery of an active ingredient may potentially be used to treat a variety of animal conditions and physical states. These systems may potentially have particular application to pain management, namely the treatment and alleviation of pain associated with any disease condition or physical state.

Without being limited to the specific pain being treated, the preparations of this invention when formulated with an active ingredient for sustained delivery of an active ingredient may potentially treat the following non-limiting locations or sources of pain: abdominal, such as in appendicitis, dysmenorrhea, musculoskeletal, pelvic, peptic ulcer, psychogenic, and urologic; acute; arm; backache; cancer; cardiac (myocardial ischemia); chest; dental; ear; esophageal; eye; face; head; and neck; in fibromyalgia; foot; and leg; heel; ischemic pain such as in myocardial, peripheral arterial, low back, in mitral valve prolapse, in myocardial infarction, myofascial pain syndrome (fibromyalgia, fibromyositis), neck, neuropathic, neurotransmitter abnormality, nociceptive, and nocturnal pain; pelvic; pericardial; in peripheral arterial disease; phantom limb; pleuritic; polyneuropathy; postmastectomy syndrome; postoperative; psychogenic; in pulmonary embolism; in renal disease, such as colic; root avulsions; shoulder; stump; thalamic; in toes; and toothache.

Besides chronic and intractable pain where injections of the formulation of the present invention for sustained delivery of an active ingredient may be required, the present sustained delivery formulations may potentially be used to aid in post-surgical pain treatments. With regard to uses after surgery, the formulations may be used following abdominal, cervical, thoracic or cardiac surgery, whereby multiple layers of tissue, as being sewed back together, are treated with the system. Such treatments may aid in a patient's recovery by not only avoiding addictive drug use such as a morphine drip, but result in the immediate and long term relief of pain to enable rapid rehabilitation.

The formulations of the present invention are formulated into pharmaceutically acceptable dosage forms by conventional methods known in the pharmaceutical art.

An effective but nontoxic amount of the system is employed in treatment. The dose regimen for administering drugs or treating various conditions may be selected in accordance with a variety of factors including the type, age, weight, sex, and medical condition of the subject, the route of administration and the particular formulation or combination of active ingredients employed. Determination of the proper dose for a particular situation is within the skill of the art. Generally, amounts of the active ingredient may vary from 0.0001% to about 50% by weight of the system.

The bio-fermented sodium hyaluronate polymer matrix formulation of the present invention was found to be stable and safer than that used in the known Ionic Polymer Matrix (IPM) Wound Gel based on various testing such as Bacterial Endotoxin Test (BET), biocompatibility tests (Example 1, Example 2, and Example 3) and microbial bio-burden test (Example 7), and is of better quality based on validated chemical test (Example 5 and 6) and stability data of the product at regular interval of time (Example 4).

A new BET has been carried out in addition to the existing test methods used with the Ionic Polymer Matrix (IPM) Wound Gel product in order to ensure that the bio-fermented sodium hyaluronate polymer matrix formulation of the present invention meets the acceptable BET test limits and hence potentially reduces the incidence of pyrogenicity in the patients. Previously, there were no BET test limits set for the Ionic Polymer Matrix (IPM) Wound Gel product. Only positive or negative bacterial endotoxin test results were identified. The BET test results carried out with the bio-fermented sodium hyaluronate polymer matrix formulation product and bio-fermented sodium hyaluronate raw material indicated that the products pass the BET test. Both the raw material bio-fermented sodium hyaluronate and the finished bio-fermented sodium hyaluronate polymer matrix formulation product were tested for BET with stringent limits. The BET test were validated.

In addition, no microbiological tests for specific microorganisms or the absence of specific microorganisms were previously performed on the Ionic Polymer Matrix (IPM) Wound Gel product. Microbiological testing performed on each batch or lot of the bio-fermented sodium hyaluronate polymer matrix formulation product included all the tests as per USP<61> (Total Aerobic Microbial Count (TAMC) and Total Combined Yeast and Mould Count (TYMC)) and USP<62> (Absence of *Staphylococcus aureus*, *Pseudomonas aeruginosa*, *E. coli* and *Salmonella*). The product passed these tests. The stability of the bio-fermented sodium hyaluronate polymer matrix formulation has now also been investigated and the product has demonstrated acceptable stability.

Previous the test methods used for the determination of sodium hyaluronate and methylparaben in the Ionic Polymer Matrix (IPM) Wound Gel product were found to be not precise, accurate or linear since the test methods were not validated. Validated analytical test methods were also developed and applied to the determination of hyaluronic acid content (see Example 13 and Example 5) and also for the determination of methylparaben content (see Example 14 and Example 6) in the bio-fermented sodium hyaluronate polymer matrix formulation.

Application of the bio-fermented sodium hyaluronate polymer matrix formulation was shown in a clinical study showing improvement in closure of incision lines in patients with toe amputations due to diabetes complications (Example 8).

In summary, the disclosed process allows for preparing sodium hyaluronate polymer matrix concentration having a high concentration of sodium hyaluronate, i.e., from about 1.5% to about 3.5% w/w. There is a significant improvement in the quality and safety of bio-fermented sodium hyaluronate polymer matrix formulation from the known Ionic Polymer Matrix (IPM) Wound Gel due to the change in the source of sodium hyaluronate from avian (rooster comb) to a bio-fermented source obtained from a bacterial fermentation process. Specifically, the stability of the compositions of the present invention, and the wound-healing properties of the compositions of the present invention are significantly and unexpectedly improved, and the cytotoxicity of the compositions of the present invention is reduced, over compositions comprising natural sodium hyaluronate from avian sources. The use of compendial and/or or pharmaceutical grade raw materials has also been unexpectedly found to further improve the stability, reduce cytotoxicity, and improve wound-healing properties of the compositions.

The improvements are evident from the development and application of additional quality testing such as BET and bioburden test (USP 62) and improved Biocompatability test (Cytotoxicity test) results, the development and application of test methods for sodium hyaluronate and the preservative methylparaben.

Table 2 below summarizes the testing regimen of the formulation of the present invention in comparison to the testing regimen of IPM Would Gel.

TABLE 2

Summary of the testing regimen of the formulation of the present invention in comparison to the testing regimen of IPM Would Gel.

| IPM Wound Gel | Sodium hyaluronate bio-fermented formulation of the present invention |
|---|---|
| Bacterial Endotoxin Test | |
| BET: Negative The test method was based old Rabbit Pyrogenicity test. — | BET test limits established. The test method is based on LAL test (Limulus amebocyte lysate test) method which is better quantified. BET method validated |
| Test for Specified Microorganisms | |
| — | Test for Specified Microorganisms including: *Pseudomonas aeruginosa*: Negative *Staphylococcus aureus*: Negative *E. coli*: Negative *Salmonella*: Negative Conducted per USP<62>/Ph. Eur. |
| Validated Test Methods | |
| — | Analytical test method validated for the determination of sodium hyaluronate content in the sodium hyaluronate bio-fermented formulation. |
| — | Analytical test method validated for the determination of methylparaben content in the sodium hyaluronate biofermented formulation. |
| Viscosity | |
| — | Viscosity (η) = 10, 000-50,000 cps (recorded). |
| Anti-microbial Effectiveness Test (AET) | |
| — | AET: Meets USP requirements (stability test) (USP <51>) |
| Methylparaben test | |
| — | Methylparaben test (Limit 90-10%) (stability test) |
| Biocompatibility Test | |
| Test for Skin Irritation, Guinea pig Maximization Sensitization Test and Cytotoxicity Test were performed. | Test for Skin Irritation, Guinea pig Maximization Sensitization Test and Cytotoxicity Test were performed. However, Cytotoxicity test showed that the test article had a smaller zone of lysis (i.e. less cytotoxic) as compared to the IPM Wound Gel. |
| Stability | |
| 1 year long-term stability tested. | 18 months long-term stability tested. |

In the examples below, results of testing of bio-fermented sodium hyaluronate polymer matrix formulation comprising sodium hyaluronate (2.5%, w/w), hydroxyethyl cellulose (1% w/w), methylparaben (0.2% w/w), polyethylene glycol (3%, w/w) and purified water, USP (approx. 93%, w/w) made from raw materials of preferred grades and by preferred process of the present invention (referred to as the "test article", also referred to "IPM Wound Gel Bio") are presented.

Example 1: Test for Skin Irritation

The test article, bio-fermented sodium hyaluronate polymer matrix formulation was evaluated for primary skin irritation in accordance with the guidelines of ISO 10993-10, Biological evaluation of medical devices—Part 10: Tests for irritation and skin sensitization.

Two 0.5 mL portions of the test article and control article (namely, saline solution, i.e., 0.9% Sodium chloride solution) were topically applied to the skin of each of three rabbits and left in place for 24 hours. The sites were graded for erythema and edema at 1, 24, 48 and 72 hours after removal of the single sample application.

There was no erythema and no edema observed on the skin of the animals treated with the test article. The Primary Irritation Index for the test article was calculated to be 0.0. The response of the test article was categorized as negligible.

Example 2: Guinea Pig Maximization Sensitization Test

The test article was evaluated for the potential to cause delayed dermal contact sensitization in a guinea pig maximization test. This study was conducted based on the requirements of ISO 10993-10, Biological evaluation of medical devices—Part 10: Tests for irritation and skin sensitization. Dose determination was performed to determine a suitable test article concentration for testing. The test article solution was intradermally injected and occlusively patched to ten test guinea pigs. The control article was similarly injected and occlusively patched to five control guinea pigs. Following a recovery period, the test and control animals received challenge patches of the test solution and the vehicle control article. All sites were scored for dermal reactions at 24 and 48 hours after patch removal.

The test article solution showed no evidence of causing delayed dermal contact sensitization in the guinea pig. The test article was not considered a sensitizer in the guinea pig maximization test.

Example 3: Cytotoxicity Test

The in-vitro cytotoxicity test showed that the test article had a smaller zone of lysis (i.e. less cytotoxic) as compared to the previous known Ionic Polymer Matrix (IPM) Wound Gel. The details of the test performed is provided below:

The test article was evaluated to determine the potential for cytotoxicity based on the requirements of ISO 10993-5: Biological evaluation of medical devices—Part 5: Tests for in vitro cytotoxicity. Triplicate wells were dosed with 0.1 mL of the test article placed on a filter (test filter disc). Triplicate wells were dosed with 0.1 mL of 0.9% sodium chloride solution placed on a filter disc (filter disc control). Triplicate wells were dosed with a 1 cm length portion of high density polyethylene as a negative control.

Triplicate wells were dosed with a 1 cm×1 cm portion of latex as a positive control. Each was placed on an agarose surface directly overlaying a sub confluent monolayer of L-929 mouse fibroblast cells. After incubating at 37° C. in the presence of 5% $CO_2$ for 24 hours, the cultures were examined macroscopically and microscopically for any abnormal cell morphology and cell lysis.

The in-vitro cytotoxicity test showed that the test article had a smaller zone of lysis (i.e., less cytotoxic) as compared to the previously known Ionic Polymer Matrix (IPM) Wound Gel, as shown in Table below.

|  | Zone of lysis (mm) | |
| --- | --- | --- |
|  | Test article | IPM Wound Gel |
| Test Disc 1 | 1 | 4 |
| Test Disc 2 | 1 | 4 |
| Test Disc 2 | 1 | 4 |

Example 4: Stability of Bio-Fermented Sodium Hyaluronate Polymer Matrix Formulation Stability of the test article was studied after incubation at various temperatures and time-intervals.

Methods: The concentrations of sodium hyaluronate were measured after incubation periods of various lengths. Other test parameters included appearance test, methylparaben assay, pH and viscosity.

Results: Examples of test results for IPM Wound Gel Bio are shown in

TABLE # 3a

All concentrations of sodium hyaluronate are in % w/w.

| | Sodium hyaluronate % (w/w) | | |
| --- | --- | --- | --- |
| Temperature | Month 0 | Month 3 | Month 6* |
| 25° C. and 60% RH | 2.48 | 2.51 | 2.52 |
| 30° C. and 65% RH | 2.48 | Not Scheduled | 2.53 |
| 30° C. and 75% RH | 2.48 | 2.47** | 2.55 |
| 40° C. and 75% RH | 2.48 | 2.52 | 2.46 |

*It has been seen that the response factor of the calibration curve increase during the stability study. This is probably due to absorption of water for the standard. The response factor has increased to 104% from the zero value to the six months value (103% from zero to three months). The results are therefore false higher.
**% RSD for 2 in weights (4 injections) 4.25%.

All other test parameters were all well within the stability test limits. Further exemplary long-term (18 month) stability test results relating to IPM Wound Gel Bio are provided in Table 1b. The concentration of sodium hyaluronate is expressed as a percentage of the original amount. The tests were performed under standard conditions (25° C. and 60% RH).

TABLE 3b

| | Time (months) | | | | | |
| --- | --- | --- | --- | --- | --- | --- |
| | 0 | 3 | 6 | 9 | 12 | 18 |
| Amount of sodium hyaluronate | 96.7% | 91.4% | 93.1% | 93.2% | 93.4% | 94.4% |

Conclusions: It can be concluded from the results presented above that the test article is stable over a prolonged period as substantiated by the results from the accelerated stability tests at 40° C. and 75% RH, and by the results from the long-term stability tests. In contrast, the control product comprising avian sodium hyaluronate (IPM Wound Gel) failed stability tests conducted after 6 months.

Example 5: Method Validation of Determination of Sodium Hyaluronate Content in the Test Article An HPLC method was developed and validated for the determination sodium hyaluronate in the test article. An HPLC System with a UV detector was used.

Results and Discussion: The average assay obtained for sodium hyaluronate in the test article was 2.545% w/w and the % relative standard deviation was 0.32. Over a range of 1.14% (or 114 µg/mL) to 3.99% (or 399 µg/mL) the assay showed good linearity with a correlation coefficient greater than 0.999. A precision study showed that the % relative standard deviation was approximately 0.481 for the % Label claim of sodium hyaluronate. Hence the HPLC method used for the determination of sodium hyaluronate content (or assay) has been validated and verified.

Example 6: Method Validation for the Determination of Methylparaben Content in the Test Article An HPLC method was validated for the determination methylparaben content in the test article was developed. An HPLC System with a UV detector was used.

Results and Discussion: The average assay obtained for methylparaben was 103.3% and the % relative standard deviation was 0.56. Over a range of 0.06% to 0.18% the assay of methylparaben showed good linearity with a correlation coefficient greater than 0.999. A precision study showed that the % relative standard deviation was approximately 0.096 for the Label claim of methylparaben. Hence the HPLC method used for the determination of methylparaben content (or assay) has been validated and verified.

Example 7: Antimicrobial Effectiveness Testing (AET)

Antimicrobial efficacy testing (AET) measures the effectiveness of antimicrobial preservatives that are added to inhibit the growth of microorganisms that may be introduced inadvertently during the manufacturing process or during product use. Antimicrobial effectiveness testing should be performed on all aqueous-based products that are injectable, ophthalmic, otic, nasal, oral, and topical.

The antimicrobial preservative in the test article is methylparaben at target concentration of 0.2% w/w.

Methods: The AET was performed on the test article as per USP<51> compendial standard using the all five microorganisms—*Escherichia coli* (fermentative gram negative bacteria), *Pseudomonas aeruginosa* (non-fermentative gram negative bacteria), *Staphylococcus aureus* (gram positive bacteria), *Aspergillus niger* (mold or fungus) and *Candida albicans* (yeast). The Antimicrobial Effectiveness Testing was performed on three lots at 18 months' time-point Long-Term Stability Study.

Results: The test results indicated that the proposed preservative system and concentration met the preservative effectiveness test requirements for Category 2 products (as per USP, topically used products made with aqueous bases or vehicles, non-sterile nasal products, and emulsions, including those applied to mucous membranes). Specifically, even at 18 months, the test article was negative for *Escherichia coli, Pseudomonas aeruginosa, Staphylococcus aureus, Aspergillus niger* and *Candida albicans*. Furthermore, even at 18 months, the TYMC and TAMC were found to be less than 10 cfu/g. In contrast, the control product comprising avian sodium hyaluronate (IPM Wound Gel) failed microbial tests after 6 months.

Conclusion: The preservative system has been demonstrated to be suitable and effective in protecting the test article from microbial growth or from inadvertently introduced microorganisms.

Example 8: Closure of Incision Lines in Patients with Digit Amputations

Study design: IPM Wound Gel Bio was used in the healing of incision lines after digit amputations. Over a period of 9 months, 116 amputations were performed on diabetic patients with non-healing, digital diabetic ulceration. Blood supply was never perfect in those patients, however, is also not profoundly impaired. The treatment protocol was to apply a thin film of IPM Wound Gel Bio along the incision line, on a daily basis, with the wound site covered with foam dressing. The patients were seen 1 week postoperatively and again 2 weeks later.

Results: The results that 94 (81%) of those patients healed, with complete epithelialization of the incision line within 1-2 weeks. This is in contrast to a typical 4 week healing time that was observed prior to using IPM Wound Gel Bio. In addition, the complication rate was correspondingly low as there was no incision line dehiscence or infection.

Conclusions: The overall experience with IPM Wound Gel Bio has been extremely positive. Particularly striking was the consistency in the healing times of the incision lines, given that the patients were very sick patients with profound underlying end organ damage. The healing mechanism in these individuals is grossly impaired and amputation with primary closure is frequently fraught with postoperative complications. The rate of these complications was reduced with the introduction of IPM Wound Gel Bio as a postoperative treatment protocol and as such the need for ongoing homecare was reduced as well the patient's return to work or normal activities of daily living was accelerated. The improved wound healing properties of IPM Wound Gel Bio may be attributable to the increased stability and reduced cytotoxicity of IPM Wound Gel Bio.

Example 9: A Formulation Containing Sodium Hyaluronate for Application to Wounds

TABLE 3

A preferred biofermented sodium hyaluronate formulation containing a high concentration sodium hyaluronate

| Ingredient | Amounts (% w/w) |
| --- | --- |
| Sodium hyaluronate | 2.5 |
| Hydroxyethylcellulose | 1.0 |
| Polyethylene glycol | 3.0 |
| Methylparaben | 0.2 |
| Water | q.s.* |
| Total | 100 |

*quantum sufficit

The above batch contained a sodium hyaluronate as a humectant and matrix forming agent, hydroxyethylcellulose is a thickening agent and helps in forming polymer matrix, polyethylene glycol is a solvent, methylparaben as preservative and water as a solvent. Several experiments were done and the optimum pH range was established to be 5.0 to 7.0. The optimum viscosity range of the solution was established to be in the range of 10,000-50,000 cps at room temperature (23° C.). The product is found to be stable.

The formulation in Table 1 was prepared by adding methylparaben to water in a suitable container and mixing at a speed of from about 400 rpm to less than about 2000 rpm ("medium speed") for a few hours (about 2 hours). Ensure that methylparaben is completely dissolved. Then slowly add sodium hyaluronate (having a molecular weight from 600,000-800,000 Daltons) in a steady flow to the mixture gradually increasing the stirring speed from medium speed as defined above to a speed of from about 2000 rpm to about 3000 rpm ("high speed") as the mixture thickens and the spin stays while charging sodium hyaluronate in a suitable container (for about 1 hour). Mix for few hours (about 2 hours) at medium speed. Continue the mixing at a speed of from about 25 rpm to less than 400 rpm ("low speed") for long duration (about 8 hours) until all of the sodium hyalorunate polymer has dissolved into the mixture and a crystal-clear viscous solution has formed.

In a separate container dissolve 1% hydroxyethylcellulose in purified water while stirring at medium speed and mix well. Continue stirring for few hours (from about 1 to about 2 hours).

The resulting hydroxyethylcellulose solution is added to the sodium hyaluronate solution and mixed at medium speed followed by low speed for long period (about 4 hours) until a homogenous solution is produced.

Add polyethylene glycol into the mixture while mixing at a medium speed. Continue mixing at medium speed for about 1 hour. Reduce the speed and continue mixing at low speed for a few hours (minimum of about 3 hours). The bulk gel is then filled in tubes or bottles and capped.

Example 10: A Formulation Containing Sodium Hyaluronate and Pantothenic Acid for Topical Use A formulation containing sodium hyaluronate and pantothenic acid may be used in the treatment of damaged skin and can be used in the treatment of atopic dermatitis.

TABLE 4

A biofermented sodium hyaluronate formulation containing a high concentration sodium hyaluronate and pantothenic acid.

| Ingredient | Amounts (% w/w) |
| --- | --- |
| Sodium hyaluronate | 1.5 |
| Hydroxyethylcellulose | 1.0 |
| Polyethylene glycol | 3.0 |
| Pantothenic acid (Vitamin B5) | 1.5 |
| Methylparaben | 0.2 |
| Water | q.s.* |
| Total | 100 |

*quantum sufficit

The formulation in Table 2 was prepared as detailed below:

First, add methylparaben to water in a suitable container and mix at medium speed for few hours (about 2 hours). Ensure that methylparaben is completely dissolved. Then add sodium hyaluronate slowly in a steady flow in water while gradually increasing the stirring speed from medium to high speed as the dissolvent thickens and the spin stays while charging sodium hyaluronate in a suitable container. Mix for few hours (about 2 hours) at medium speed. Continue the mixing at low speed for long duration (overnight, or about 8 hours to about 15 hours) until all of the sodium hyalorunate polymer has dissolved into the mixture and a crystal-clear viscous solution has formed.

In a separate container dissolve 1.0% hydroxyethylcellulose in purified water while stirring at medium speed and mix well. Continue stirring for a few hours (from about 1 to about 2 hours).

Next the hydroxyethylcellulose solution is added to the sodium hyaluronate solution and mixed at medium speed until a homogenous solution is produced. The resulting solution is mixed at medium speed for long period (overnight, or about 8 hours to about 15 hours) until a homogenous solution is produced. Add polyethylene glycol into the mixture while mixing at a medium speed for about 1 hour. This is followed by the addition of pantothenic acid and mixing well at medium speed for few hours (about 2 hours) until dissolved and the gel is homogeneous. The bulk gel is then filled in tubes or bottles and capped.

Example 11: A Formulation Containing Sodium Hyaluronate and Diclofenac Sodium for Topical Use A formulation containing sodium hyaluronate and diclofenac sodium can be used to treat actinic keratosis and in the relief of musculoskeletal pain in areas affected by the pain. Such areas include, but are not limited to, knees, ankles, feet, back, neck, elbows and hips.

TABLE 5

A biofermented sodium hyaluronate formulation containing a high concentration sodium hyaluronate and dicloflenac sodium. The formulation was found to be stable.

| Ingredient | Amounts (% w/w) |
| --- | --- |
| Dicloflenac sodium | 3 |
| Sodium hyaluronate | 2.3 |
| Hydroxyethylcellulose | 0.7 |
| Methoxypolyethylene glycol | 10 |
| Methylparaben | 0.3 |
| Water | q.s.* |
| Total | 100 |

*quantum sufficit

The formulation in Table 3 was prepared as follows: First, add methylparaben to water in a suitable container and mix at medium speed for few hours (about 2 hours). Ensure that methylparaben is completely dissolved. Then slowly add sodium hyaluronate to it while gradually increasing the stirring speed from medium to high as the mixture thickens and the spin stays while charging sodium hyaluronate in a suitable container for about 1 hour. Mix for few hours (about 2 hours) at medium speed. Continue the mixing at low speed for long duration (about 8 hours) until all of the sodium hyaluronate polymer has dissolved into water and a crystal-clear viscous solution has formed. The gel should be homogenous.

In a separate container dissolve 0.7% hydroxyethylcellulose in purified water while stirring at low to medium speed and mix well. Continue stirring for few hours (from about 1 to about 2 hours).

The resulting hydroxyethylcellulose solution is added to the sodium hyaluronate solution and mixed at medium speed for a long period (from about 10 to about 15 hours) until a homogenous solution is produced.

Add methoxypolyethylene glycol (MPEG) 10% into the mixture. The mixing speed should be increased for the mixture while this step is being performed to a high speed. The resulting mixture thus formed should be allowed to mix at medium speed for a few hours (from about 3 to about 4 hours).

Using safe techniques, 3% diclofenac sodium should be slowly added to the mixture. Again the mixing speed for the purpose of addition of diclofenac should be increased to high speed, and the addition of entire quantity of diclofenac should be completed within a short duration (about 15 minutes).

The final mixture is clear with a slight green tint following further mixing for long duration (about 15 to about 20 hours) at medium speed. The final product should be transferred, using aseptic technique, to a bulk storage container and then the bulk gel is filled in tubes or bottles and capped.

Example 12: A Formulation Containing Sodium Hyaluronate for Treating Vaginal Dryness Containing Using Niacin and Glycerin

TABLE 6

A biofermented sodium hyaluronate formulation containing a high concentration sodium hyaluronate and niacin and glycerin.

| Ingredient | Amounts (% w/w) |
| --- | --- |
| Niacin | 0.85 |
| Glycerin | 3 |
| Sodium hyaluronate | 1.5 |
| Hydroxyethylcellulose | 0.7 |
| Polyethylene glycol | 3 |
| Methylparaben | 0.2 |
| Water | q.s.* |
| Total | 100 |

*quantum sufficit
**Glycerin USP should be used [Not More Than 0.10% each for diethylene glycol and ethylene glycol is found in Glycerin as per USP]

A transdermal preparation of niacin (0.85%) and glycerin (3%) formula for Table 4 is prepared in the following manner. First, add methylparaben to water in a suitable container and mix at medium speed for few hours (about 2 hours). Ensure that methylparaben is completely dissolved. Then add sodium hyaluronate slowly in a steady flow in water while gradually increasing the stirring speed from medium to high speed as the mixture thickens and the spin stays while charging sodium hyaluronate in a suitable container for about 1 hour. Mix for few hours (about 2 hours) at medium speed. Continue the mixing at low speed for long duration (overnight, or about 8 hours to about 15 hours) until all of the sodium hyaluronate polymer has dissolved into water and a crystal-clear viscous solution has formed. The gel should be homogenous.

Next, a solution is prepared by adding 0.7% HEC to purified water while stirring at low to medium speed and mixing well. Continue stirring for few hours (from about 1 to about 2 hours). The resulting solution is then added to the above formed mixture of sodium hyaluronate and mixed at medium speed for a long period (overnight, or about 8 hours to about 15 hours) to form a sodium hyaluronate/HEC polymer matrix.

To the resulting mixture PEG is added and stirred at medium speed for a few hours (about 2.5 hours).

Then, niacin and glycerin is added to the HA/HEC polymer matrix. The mixture is stirred at low speed for few hours (about 2 hours). The bulk gel is either stored for filling or a 0.5 to 0.75 ml of the resulting gel is loaded into syringes and stored in a refrigerator.

Example 13: Test Method for Determination of Sodium Hyaluronate

An HPLC test method for the determination of sodium hyaluronate in the test article (sodium hyaluronate bio-fermented wound gel formulation) was developed.

| | |
|---|---|
| Column | BioSep SEC-s2000, 300 mm × 7.8 mm, 5μ |
| Detection | UV @205 nm |
| Column Temp.: | 40° C. |
| Injection Volume: | 10 μL |
| Flow Rate: | 1.3 mL/min |
| Run Time: | 20 min |
| Mobile Phase: | 50 mM $KH_2PO_4$, pH adjusted to 7.0 |

The assay is based on HPLC analysis with a size exclusion analytical column and UV detection at 205 nm.

Example 14: Test Method for Determination of Methylparaben

An HPLC test method for the determination of methylparaben in the test article (sodium hyaluronate bio-fermented wound gel fog ululation) was developed.

| | |
|---|---|
| Column | Kinetex, C8, 100 mm × 4.6 mm, 2.6μ, 100 A |
| Detection | UV @254 nm |
| Column Temp.: | 35° C. |
| Injection Volume: | 20 μL |
| Flow Rate: | 1.4 mL per min |
| Run Time: | 2 min |
| Mobile Phase: | 60:40 (v/v) 0.1% TFA in Milli-Q Water; 0.1% TFA in Acetonitrile |

The assay is based on HPLC analysis with reverse phase C8 analytical column and UV detection at 254 nm.

Although specific embodiments of the invention have been described, it will be apparent to one skilled in the art that variations and modifications to the embodiments may be made within the scope of the following claims.

Example 15: Pharmacokinetics and Bioavailability of 3% Diclofenac IPM Matrix 2.3% Sodium Hyaluronate Gel An open label, single centre, single dose, single dose, one-treatment, one period, pharmacokinetic and bioavailability study was carried out. Six normal, healthy, non-smoking males between the ages of 18-45 were administered 3% diclofenac IPM matrix gel made with 2.3% avian sodium hyalorunate, which was applied once for a 24 hour period. A total of 4 cc was the applied to the anterior right knee of each subject. Pharmacokinetics and bioavailability of the single dose application was assessed. A total 18 blood samples and 8 urine samples were collected for each subject during the 24 hour period after administration. The concentration of diclofenac was assessed for each sample. Diclofenac plasma and urine concentrations are presented in Table 7 and 8. Diclofenac was found in samples from all subjects. Concentrations varied from subject to subject, but this was normal for diclofenac.

TABLE 7

Diclofenac Plasma Concentration (ng/mL) Measured in Samples from Subjects Using 3% Diclofenac Gel

| Subject | Hour | Min | Diclofenac Concentration Found [ng/ml] |
|---|---|---|---|
| 1 | 0 | 0 | BLQ |
| 1 | 0 | 25 | BLQ |
| 1 | 0 | 5 | BLQ |
| 1 | 0 | 75 | BLQ |
| 1 | 1 | 0 | 0.074 |
| 1 | 1 | 5 | 0.228 |
| 1 | 2 | 0 | 0.385 |
| 1 | 2 | 5 | 0.487 |
| 1 | 3 | 0 | 0.655 |
| 1 | 3 | 5 | 0.859 |
| 1 | 4 | 0 | 0.807 |
| 1 | 5 | 0 | 0.944 |
| 1 | 6 | 0 | 1.40 |
| 1 | 7 | 0 | 1.53 |
| 1 | 8 | 0 | 1.75 |
| 1 | 12 | 0 | 1.57 |
| 1 | 16 | 0 | 1.93 |
| 1 | 24 | 0 | 2.33 |
| 2 | 0 | 0 | BLQ |
| 2 | 0 | 25 | BLQ |
| 2 | 0 | 5 | BLQ |
| 2 | 0 | 75 | BLQ |
| 2 | 1 | 0 | 0.042 |
| 2 | 1 | 5 | 0.191 |
| 2 | 2 | 0 | 0.369 |
| 2 | 2 | 5 | 0.403 |
| 2 | 3 | 0 | 0.471 |
| 2 | 3 | 5 | 0.410 |
| 2 | 4 | 0 | 0.496 |
| 2 | 5 | 0 | 0.814 |
| 2 | 6 | 0 | 1.03 |
| 2 | 7 | 0 | 1.01 |
| 2 | 8 | 0 | 1.33 |
| 2 | 12 | 0 | 1.25 |
| 2 | 16 | 0 | 1.98 |
| 2 | 24 | 0 | 2.44 |
| 3 | 0 | 0 | BLQ |
| 3 | 0 | 25 | BLQ |
| 3 | 0 | 5 | BLQ |
| 3 | 0 | 75 | BLQ |
| 3 | 1 | 0 | BLQ |
| 3 | 1 | 5 | BLQ |
| 3 | 2 | 0 | 0.049 |
| 3 | 2 | 5 | 0.184 |
| 3 | 3 | 0 | 0.118 |
| 3 | 3 | 5 | 0.184 |
| 3 | 4 | 0 | 0.232 |
| 3 | 5 | 0 | 0.244 |
| 3 | 6 | 0 | 0.377 |
| 3 | 7 | 0 | 0.489 |
| 3 | 8 | 0 | 0.532 |
| 3 | 12 | 0 | 0.944 |
| 3 | 16 | 0 | 1.64 |
| 3 | 24 | 0 | 2.92 |
| 4 | 0 | 0 | BLQ |
| 4 | 0 | 25 | BLQ |
| 4 | 0 | 5 | BLQ |
| 4 | 0 | 75 | BLQ |
| 4 | 1 | 0 | BLQ |
| 4 | 1 | 5 | BLQ |
| 4 | 2 | 0 | BLQ |
| 4 | 2 | 5 | 0.090 |
| 4 | 3 | 0 | BLQ |
| 4 | 3 | 5 | 0.053 |
| 4 | 4 | 0 | 0.045 |
| 4 | 5 | 0 | 0.084 |
| 4 | 6 | 0 | 0.107 |
| 4 | 7 | 0 | 0.312 |
| 4 | 8 | 0 | 0.383 |
| 4 | 12 | 0 | 0.563 |
| 4 | 16 | 0 | 0.940 |
| 4 | 24 | 0 | 0.429 |
| 5 | 0 | 0 | BLQ |
| 5 | 0 | 25 | BLQ |

TABLE 7-continued

Diclofenac Plasma Concentration (ng/mL) Measured in Samples from Subjects Using 3% Diclofenac Gel

| Subject | Hour | Min | Diclofenac Concentration Found [ng/ml] |
|---|---|---|---|
| 5 | 0 | 5 | BLQ |
| 5 | 0 | 75 | BLQ |
| 5 | 1 | 0 | BLQ |
| 5 | 1 | 5 | BLQ |
| 5 | 2 | 0 | BLQ |
| 5 | 2 | 5 | 0.046 |
| 5 | 3 | 0 | 0.066 |
| 5 | 3 | 5 | 0.081 |
| 5 | 4 | 0 | 0.150 |
| 5 | 5 | 0 | 0.367 |
| 5 | 6 | 0 | 0.448 |
| 5 | 7 | 0 | 0.742 |
| 5 | 8 | 0 | 1.07 |
| 5 | 12 | 0 | 3.04 |
| 5 | 16 | 0 | 3.65 |
| 5 | 24 | 0 | 2.17 |
| 6 | 0 | 0 | BLQ |
| 6 | 0 | 25 | BLQ |
| 6 | 0 | 5 | BLQ |
| 6 | 0 | 75 | BLQ |
| 6 | 1 | 0 | BLQ |
| 6 | 1 | 5 | 0.023 |
| 6 | 2 | 0 | 0.072 |
| 6 | 2 | 5 | 0.109 |
| 6 | 3 | 0 | 0.215 |
| 6 | 3 | 5 | 0.287 |
| 6 | 4 | 0 | 0.385 |
| 6 | 5 | 0 | 0.772 |
| 6 | 6 | 0 | 1.23 |
| 6 | 7 | 0 | 1.60 |
| 6 | 8 | 0 | 1.98 |
| 6 | 12 | 0 | 1.34 |
| 6 | 16 | 0 | 1.63 |
| 6 | 24 | 0 | 1.31 |

*BLQ = below the lower limit of quantification (0.02 ng/ml)

TABLE 8

Diclofenac Urine Concentration (ng/mL) Measured in Samples from Subjects Using 3% Diclofenac Gel

| Subject | Hour | Diclofenac Concentration Found [ng/ml] |
|---|---|---|
| 1 | pre 0.0 hr | BLQ |
| 1 | 0.0-2.0 hr | 0.012 |
| 1 | 2.0-4.0 hr | 0.117 |
| 1 | 4.0-6.0 hr | 0.704 |
| 1 | 6.0-8.0 hr | 3.58 |
| 1 | 8.0-10.0 hr | 3.98 |
| 1 | 10.0-12.0 hr | 3.83 |
| 1 | 12.0-24.0 hr | 2.81 |
| 2 | pre 0.0 hr | BLQ |
| 2 | 0.0-2.0 hr | 0.042 |
| 2 | 2.0-4.0 hr | 0.434 |
| 2 | 4.0-6.0 hr | 0.428 |
| 2 | 6.0-8.0 hr | 0.724 |
| 2 | 8.0-10.0 hr | 2.59 |
| 2 | 10.0-12.0 hr | 0.785 |
| 2 | 12.0-24.0 hr | 2.67 |
| 3 | pre 0.0 hr | BLQ |
| 3 | 0.0-2.0 hr | BLQ |
| 3 | 2.0-4.0 hr | BLQ |
| 3 | 4.0-6.0 hr | 0.144 |
| 3 | 6.0-8.0 hr | 0.315 |
| 3 | 8.0-10.0 hr | 0.748 |
| 3 | 10.0-12.0 hr | 0.427 |
| 3 | 12.0-24.0 hr | 6.04 |
| 4 | pre 0.0 hr | BLQ |
| 4 | 0.0-2.0 hr | BLQ |

TABLE 8-continued

Diclofenac Urine Concentration (ng/mL) Measured in Samples from Subjects Using 3% Diclofenac Gel

| Subject | Hour | Diclofenac Concentration Found [ng/ml] |
|---|---|---|
| 4 | 2.0-4.0 hr | 0.051 |
| 4 | 4.0-6.0 hr | 0.120 |
| 4 | 6.0-8.0 hr | 0.356 |
| 4 | 8.0-10.0 hr | 0.654 |
| 4 | 10.0-12.0 hr | 4.95 |
| 4 | 12.0-24.0 hr | 2.24 |
| 5 | pre 0.0 hr | BLQ |
| 5 | 0.0-2.0 hr | 0.595 |
| 5 | 2.0-4.0 hr | 0.097 |
| 5 | 4.0-6.0 hr | 0.804 |
| 5 | 6.0-8.0 hr | 2.29 |
| 5 | 8.0-10.0 hr | 0.763 |
| 5 | 10.0-12.0 hr | 3.28 |
| 5 | 12.0-24.0 hr | 7.76 |
| 6 | pre 0.0 hr | BLQ |
| 6 | 0.0-2.0 hr | BLQ |
| 6 | 2.0-4.0 hr | 0.384 |
| 6 | 4.0-6.0 hr | 3.52 |
| 6 | 6.0-8.0 hr | 13.9 |
| 6 | 8.0-10.0 hr | 11.0 |
| 6 | 10.0-12.0 hr | 2.71 |
| 6 | 12.0-24.0 hr | 2.27 |

* BLQ = below the lower limit of quantification (0.01 ng/ml)

Example 16: Efficacy of 3% Diclofenac IPM 2.3% Sodium Hyalorunate Matrix Gel by Topical Application in Treating Painful Musculoskeletal Conditions, Principally Involving the Relief of Pain and Muscle Spasm 23 patients with musculoskeletal pain, at a pain clinic, were asked to volunteer to test 3% diclofenac IPM 2.3% sodium hyalorunate matrix gel made with avian sodium hyalorunate. The gel was applied liberally on the skin four times a day over the area with the musculoskeletal problem causing the pain. The patients were asked to assess 34 criteria to estimate their musculoskeletal pain or stiffness on a visual analogue scale, graded 0-10 at the first visit. 17 patients were assessed on only one criterion but five patients were assessed on two criteria as follows: right and left ankle, neck pain and stiffness, headache and neck pain and shoulder and neck pain to make a total of 34 criteria. They were then given a supply of diclofenac gel to apply to painful area and asked to grade the change in the pain on a nine point scale from very much worse through no change to very much better. The patients were then given a further one week supply of gel and they did a second self assessment at the end of the second week's treatment.

After one week's treatment, of 23 patients' 27 criteria, eight criteria reported no change, 19 reported an improvement varying between somewhat better and no pain and no one had worse pain. The improved group consisted of ten, one, six and two patients being respectively somewhat better, better, much better and having no pain. No patient had worse pain.

After two week's treatment, which essentially are similar to the results at one week, but one patient's criterion reported being somewhat worse, six showed no change and twenty patients' criteria reported improvement with feeling better.

Combining the results at one and two weeks produced a similar result to each of them. Using a visual analogue scale with only one criterion for each patient, the average figure falls after diclofenac and rises when it is discontinued In conclusion, diclofenac gel is an effective preparation for the transcutaneous relief of arthritis and musculoskeletal pain. It has good patient acceptance, is easily administered, causes no serious side-effects, and avoids the gastrointestinal upset that so often accompanies oral NSAID use.

There would be an expected improvement in the above-mentioned clinical behavior of ionic polymer matrix gel manufactured with sodium hyaluronate from a bacterial source in accordance with the present invention, compared with that manufactured with hyaluronate from an avian source used in example 15 and 16 since the formulations of the present invention have reduced cytotoxicity effects and improved stability.

What is claimed is:

1. A stable topical polymer matrix gel composition comprising:
   1.5% w/w to 3.5% w/w bio-fermented sodium hyaluronate;
   0.1% w/w to 2.0% w/w hydroxyethylcellulose;
   2% w/w to 4% w/w polyethylene glycol;
   0.1% w/w to 0.3% w/w methylparaben; and
   water;
   wherein the bio-fermented sodium hyaluronate is of pharmaceutical grade according to the European Pharmacopoeia, has an average molecular weight between about 600,000 Daltons to about 800,000 Daltons, has nucleic acid content of less than or equal to 0.5%, has protein content of less than or equal to 0.3%, Total Combined Yeast and Mould Count (TYMC) of less than or equal to 10 cfu/q, Bacterial Endotoxin Test (BET) score of less than or equal to 0.5 IU/mg, and tests absent for *Staphylococcus aureus, Pseudomonas aeruginosa, Escherichia coli,* and *Salmonella* sp.;
   wherein the hydroxyethylcellulose is of pharmaceutical grade and has a Total Aerobic Microbial Count (TAMC) of less than 100 cfu/g;
   wherein the polyethylene glycol (PEG) is of pharmaceutical grade, wherein the average molecular weight of the PEG is 200 and wherein the PEG has a combined ethylene glycol and diethylene glycol content of less than or equal to 0.25%, TAMC of less than 100 cfu/mL and TYMC of less than or equal to 10 cfu/mL;
   wherein the methylparaben is of pharmaceutical grade and has a TAMC of less than 100 cfu/mL and TYMC of less than or equal to 10 cfu/mL; and
   wherein the water is purified having a TAMC of less than 100 cfu/mL and a BET score of less than 0.25 EU/mL.

2. The polymer matrix composition as in claim 1, wherein 0.1 mL of the polymer matrix composition placed on a filter disc placed on an agarose surface overlaying a sub confluent monolayer of L-929 mouse fibroblasts gives a zone of lysis of about 1 mm following incubation at 37° C. in the presence of 5% $CO_2$ for 24 hours.

3. The polymer matrix composition of claim 1, wherein the bio-fermented sodium hyaluronate is present in an amount of 2.3 to 2.7% w/w, the hydroxyethylcellulose is present in an amount of 0.5 to 1.5% w/w.

4. The polymer matrix composition of claim 3, wherein the bio-fermented sodium hyaluronate is present in an amount of 2.5% w/w, the hydroxyethylcellulose is present in an amount of 1% w/w, the polyethylene glycol is present in an amount of 3.0% w/w, and the methylparaben is present in an amount of 0.2% w/w.

5. The polymer matrix composition of claim 1 for use in one or more of: a topical application, treating and/or healing wounds wherein the use comprises applying the composition topically, treating and/or promoting healing of post-operative incisions, treating and/or healing dermatological conditions, treating and/or healing burns, treating damaged skin, treating atopic dermatitis, treating vaginal dryness, treating actinic keratosis and/or treating musculoskeletal pain.

* * * * *